(12) United States Patent
Walters et al.

(10) Patent No.: US 11,578,318 B2
(45) Date of Patent: Feb. 14, 2023

(54) LARGE VOLUME EX VIVO ELECTROPORATION METHOD

(71) Applicant: Cellectis S.A., Paris (FR)

(72) Inventors: Richard E Walters, Severna Park, MD (US); Alan D King, Highland, MD (US)

(73) Assignee: CELLECTIS S.A., Paris (FR)

(*) Notice: Subject to any disclaimer, the term of this patent is extended or adjusted under 35 U.S.C. 154(b) by 1338 days.

(21) Appl. No.: 15/956,103

(22) Filed: Apr. 18, 2018

(65) Prior Publication Data

US 2018/0237765 A1    Aug. 23, 2018

Related U.S. Application Data

(63) Continuation of application No. 10/537,254, filed as application No. PCT/US2004/005237 on Mar. 15, 2004, now Pat. No. 9,982,251.

(Continued)

(51) Int. Cl.
| | |
|---|---|
| *C12N 13/00* | (2006.01) |
| *C12M 1/00* | (2006.01) |

(Continued)

(52) U.S. Cl.
CPC .......... *C12N 13/00* (2013.01); *C12M 29/20* (2013.01); *C12N 15/87* (2013.01); *H02K 1/146* (2013.01);

(Continued)

(58) Field of Classification Search
None
See application file for complete search history.

(56) References Cited

U.S. PATENT DOCUMENTS

| | | | | |
|---|---|---|---|---|
| 4,800,163 A | * | 1/1989 | Hibi ...................... | C12N 13/00 435/173.6 |
| 6,355,485 B1 | * | 3/2002 | Jaroszeski ............. | C12N 13/00 435/449 |

(Continued)

FOREIGN PATENT DOCUMENTS

WO    WO-0060065 A1  * 10/2000  ............. B01D 61/00

*Primary Examiner* — William H. Beisner
(74) *Attorney, Agent, or Firm* — Magda Carvalho (57) ABSTRACT

An object of the invention is to provide an electroporation method for treating vesicles with exogenous material for insertion of the exogenous material into the vesicles which includes the steps of: a. retaining a suspension of the vesicles and the exogenous material in a treatment volume in a chamber which includes electrodes, wherein the chamber has a geometric factor ($cm^{-1}$) defined by the quotient of the electrode gap squared ($cm^2$) divided by the chamber volume ($cm^3$), wherein the geometric factor is less than or equal to $0.1\ cm^{-1}$, wherein the suspension of the vesicles and the exogenous material is in a medium which is adjusted such that the medium has conductivity in a range spanning 50 microSiemens/cm to 500 microSiemens/cm, wherein the suspension is enclosed in the chamber during treatment, and b. treating the suspension enclosed in the chamber with one or more pulsed electric fields. With the method, the treatment volume of the suspension is scalable, and the time of treatment of the vesicles in the chamber is substantially uniform.

8 Claims, 5 Drawing Sheets

Related U.S. Application Data (60) Provisional application No. 60/454,630, filed on Mar. 17, 2003.

(51) Int. Cl.
*C12N 15/87* (2006.01)
*C12M 1/42* (2006.01)
*C12M 3/00* (2006.01)
*C12M 3/02* (2006.01)
*H02K 1/24* (2006.01)
*H02K 1/14* (2006.01)
*H02K 19/10* (2006.01)
*A61K 9/00* (2006.01)

(52) U.S. Cl.
CPC ........... H02K 1/246 (2013.01); H02K 19/103 (2013.01); *A61K 9/0009* (2013.01); *C12M 1/42* (2013.01); *C12M 3/00* (2013.01); *C12M 3/006* (2013.01); *C12M 3/02* (2013.01); *C12M 35/02* (2013.01); *C12M 45/07* (2013.01)

(56) References Cited

U.S. PATENT DOCUMENTS

| | | | |
|---|---|---|---|
| 6,358,731 B1* | 3/2002 | Hsu | C12M 29/20 435/297.5 |
| 2003/0073238 A1* | 4/2003 | Dzekunov | A61K 9/5068 435/173.6 |
| 2005/0040044 A1* | 2/2005 | Frenea | B03C 5/026 204/450 |
| 2006/0115888 A1* | 6/2006 | Gamelin | C12M 23/12 435/305.1 |

* cited by examiner

LARGE VOLUME EX VIVO ELECTROPORATION METHOD

CROSS-REFERENCE TO RELATED APPLICATION

This application claims priority to the following applications that are incorporated by reference herein: U.S. Provisional Patent Application, of Walters and King, Application No. 60/454,360, Filing Date 14 Mar. 2003, for LARGE VOLUME EX VIVO ELECTROPORATION METHOD; PCT Application of Walters and King Application Number PCT/US04/05237 filed on Mar. 15, 2004 for LARGE VOLUME EX VIVO ELECTROPORATION METHOD; and U.S. Non-provisional Application of Walters and King, application Ser. No. 10/537,254 filed on Jun. 1, 2005 for LARGE VOLUME EX VIVO ELECTROPORATION METHOD.

BACKGROUND OF THE INVENTION

Technical Field

The present invention relates generally to ex vivo electroporation methods, and, more particularly, to electroporation methods especially adapted for clinical and industrial applications.

Background Art

Delivering large molecules into living cells for therapeutic purposes, using ex vivo or in vitro electroporation, has been described in the literature for many years. The purpose of electroporation is to enhance the movement of molecules into and out of living cells or non-living vesicles. The practical uses are many and vary according to the complexity of material delivered, the site of delivery and the purpose for delivery.

Complexity ranges from small drug molecules that are otherwise difficult to get into cells to complex mixtures of polynucleotides.

The site of delivery is broadly divided into in vivo and ex-vivo delivery. The choice of an in-vivo site is based upon the location of the tissue to be treated and whether or not local or systemic treatment is desired.

Clinical and industrial applications of this process are possible. Often, in clinical and industrial applications, it is desirable to insert large molecules into large numbers of cells and to insure that all cells have been processed equally. To do that, it is desirable to process all cells simultaneously to guarantee that all cells are subjected to the same process conditions.

Therapeutic purposes for delivery are many. Some examples are gene replacement therapy, therapeutic genetic medicine for acquired diseases, polynucleotide vaccines, immunotherapy, enhanced chemotherapy and many others. Industrial and agricultural applications are equally varied. Some examples of industrial uses are extraction of material from cells produced in a fermenter, large scale transfection for production of recombinant protein, modification of cells for industrial use, sterilization of liquids or vaccine production. Some examples of agricultural uses are vaccines for livestock (to include ungulates, avian species and aquatic animals) and modification of genes for improvement of selected traits.

For standard in vitro electroporation, cuvettes are usually used. These are chambers that consist of parallel plate electrodes encased in plastic and have limited capacity. Volumes used in these cuvettes are under one milliliter. The limited volume limits the total capacity for treating cells.

Typical cell densities used are in the range of 1 million to 10 million cells per milliliter. The cells are typically placed in a physiological medium with high ionic content such as phosphate buffered saline, which has a conductivity of 0.017 Siemens/cm (which is equal to (17,000 microSiemens/cm).

In electroporation, cell density is an important parameter. If the cells are not dense enough, therapeutic or other material is wasted. If the cells are too dense the electric field in the proximity of each cell is not uniform in direction or in intensity. To produce consistent results that are required for clinical applications the electric fields close to the cells must be both uniform in direction and intensity. According to Fomekong et al in "Passive electrical properties of RBC suspensions: changes due to distribution of relaxation times in dependence on the cell volume fraction and medium conductivity", in Bioelectrochemistry and Bioenergetics, 1998, Vol 47: 81-88), the effect of cells on the electrical properties of cell suspensions is dependent upon the packed cell volume of the cells. For packed cell volumes less than 10% the distance between cells increases rapidly and therefore the interfering effect of one cell to another in the electric field decreases rapidly below a packed cell volume of 10%. A typical cell of 15 microns in diameter would be at 10% packed cell volume at approximately 60 million cells/ml (calculated using a mean cell volume of 0.000001767 mm3/cell). Thus cell densities under 60 million cells/ml should be used and normally cell densities under 30 million cells/ml are used.

TABLE 1

Electrode Chamber Volume (milliliters)

| Number of Cells Out | Number of Cells In | Cell Density | |
|---|---|---|---|
| Million/ml | Million/ml | 20 million/ml | 40 million/ml |
| 10 | 20 | 1 | 0.5 |
| 100 | 200 | 20 | 5 |
| 1000 | 2000 | 100 | 50 |

Clinical application generally requires 10 million to 500 million cells in which the large molecules have been properly inserted. If a treatment requires 10 million cells per dose (treatment) and 5 doses are required, at least 50 million therapeutic cells must be prepared. If the efficiency of the electroporation process is assumed to be 50% and cells are treated at a cell density of 20 million cells/ml then a 5 ml capacity chamber would be required (50 million×2/20 million). If 100 million therapeutic cells are required, a 10 ml capacity chamber would be needed.

Simply increasing the size of the electrodes and the chamber to achieve the desired capacity is not practical because this causes a proportionate increase in amperage due to a decrease in resistance in the electrodes and the suspension within the chamber. As the size of the electrodes and the chamber increase, the resistance of the electrodes and suspension within the chamber decreases as long as the conductivity of the suspension in the chamber remains constant.

If 100 million therapeutic cells are required and the input cell density is 20 million cells per milliliter then a 20 ml chamber is required.

In this case just scaling the size of a chamber up to 20 milliliters does not work. As the volume of a suspension within the chamber increases, the resistance of the suspension within the chamber decreases. The resistance of the suspension in the chamber is calculated as follows:

$$R = \frac{1}{\sigma} \frac{gap}{area} \text{ ohms} \qquad \text{Formula 1}$$

where s=conductivity in Siemens/cm, gap is in cm and plate area is in cm$^2$. In addition:

$$\text{volume} = gap * area \text{ cm}^3 \text{ and} \qquad \text{Formula 2}$$

$$R = \frac{1}{\sigma} \frac{gap^2}{volume} \text{ ohms} \qquad \text{Formula 3}$$

FORMULAS 1, 2, and 3 are taken from Electroporation and Electrofusion in Cell Biology, edited by Eberhard Neumann, Arthur Sowers, and Carol Jordan, Plenum Press, 1989, mentioned hereinabove.

The TABLE 2 below shows the resistance of the suspension within the chamber as a function of volume for a 4-millimeter gap and media with suspension conductivity of 0.017 Siemens/cm.

TABLE 2

| Chamber Volume (ml) | Media/Suspension Resistance (ohms) |
|---|---|
| 0.5 | 19.2 |
| 1 | 9.6 |
| 5 | 1.92 |
| 10 | 0.96 |
| 50 | 0.19 |

When the chamber volume is above 1 ml, the resistance of the ionic solution becomes impractically small; significant solution heating will occur due to the high pulse current destroying the cells.

To address this problem a flow though technique was developed. In this process the large volume of media with suspension flows through a small treatment chamber, and the voltage pulse waveform is applied to the parallel plates in the chamber. The problems with this process are:

1. Not all the cells are exposed to the same electric field intensity and direction.

2. There is no guarantee that the density of the material to be inserted and the cell density are constant.

3. Only uniform pulse voltages may be applied. Variable rectangular pulse waveforms such as disclosed in U.S. Pat. No. 6,010,613 cannot be used.

In a flow through process there is no guarantee that all cells will be subjected to the same electric field intensity and direction. In this respect, because of the properties of laminar and turbulent flow, not all of the cells will be treated for the same period of time in a flow through process. Lamina proximal to walls of flow through conduits travel slower than lamina distal to the walls. Flow through processes are used in both food processing where the electric field intensity is over 20,000 volts/cm and in inserting molecules into cells for therapeutic purposes.

A large body of prior art exists in the field of electroporation, and a number of aspects of this body of art are of particular interest herein. For example, of particular interest herein are disclosures of the electroporation medium, with special attention directed to medium parameters. In this respect, TABLE 3 herein sets forth a number of references relating to electroporation medium parameters such as cations, anions, osmolarity, and buffering.

TABLE 3

| The following table summarizes the current state of the art: | | | | | | |
|---|---|---|---|---|---|---|
| | | Cations | | | | |
| Publication | Conductivity (μs/cm) | High Conc. | Low Conc. | Anions | Osmolarity | Buffer |
| Invention | Low (50-150) | None | Ca, Mg | Organic | L-N | Histidine |
| 5,124,259 | High | K | Ca, Mg | Organic | N | |
| 6,040,184 | Very low | None | None | None | L-N | None |
| 6,338,965 | Very low | None | None | None | L-N | None |
| 6,368,784 | High | K | Ca, Mg | Cl | N | Phos, HEPES |
| Djuzenova 1996 | Moderate to high (800-14000) | Na, K | | Ca | Cl, Sulfate | N | Phos. |
| Kinosita 1977 | High | Na | | | Cl | | Phos. |
| Dimitrov 1990 | Low to Moderate | | | Na | Phos., Cl | | Phos. |
| Rols 1989 | Low and high | Na | | | Cl | | Phos. |
| Pucilar 2001 | Low and high | Na, K (if used) | | Mg | Cl, Sulfate | N | Phos. |

More particularly with respect to TABLE 3, U.S. Pat. No. 5,124,259 describes an electroporation medium that provides high transfection efficiency. The medium has potassium ions (35-105 milligram equivalents/Liter) and organic anions and is essentially devoid of chloride ions. The medium is highly conductive as a result of the potassium ions. The use of low conductive medium to allow the use of large electroporation electrodes is not discussed.

U.S. Pat. Nos. 6,040,184 and 6,338,965 describe an electroporation medium with essentially no ions. The medium is made non-ionic through the use of sugars and no inorganic ions. The patent describes increased transfection efficiency in bacteria with the non-ionic medium. The patent does not mention the addition of a small amount of organic ions to provide some conductivity and therefore some current to maintain an electric field during electroporation.

U.S. Pat. No. 6,368,784 describes an electroporation buffer that is also a cryoprotectant. It also describes the use of this material for freezing cells prior to transfection. The medium used has a high concentration of potassium ions similar to that in intracellular cytoplasm and similar to that described in U.S. Pat. No. 5,124,259. The patent does not describe the use of electroporation medium with lower conductivity to allow the use of larger capacity electrodes.

Conductivity of the medium affects the movement of material into cells. Djuezenova (Djuzenova et al, Biochemica et Biophysica Acta V 1284, 1996, p 143-152) showed that the uptake of small molecules is increased in lower conductivity medium down to 1 mS/cm, the lowest conductivity used in the study. Others have concurred that lower conductivity increases the permeability of cells to small molecules during electroporation. (Kinosita, K, Tsong, T Y, Proc. Natl. Acad Sci, USA, 1977 V74:1923-1927) (Kinosita, K, Tsong, T Y Nature, 1977 V268:438-440) (Dimitrov, D S, Sowers, A E, Biochem. Biophys. Acta. 1990, V 1022:381-392).

Kinosita found that with a given electric field, media of high conductivity allowed leakage of small ions (sodium and potassium) and medium of lower conductivity allowed passage of larger molecules (sucrose but not proteins) through red blood cell membranes. More specifically, Kinosita et al disclose hemolysis of human erythrocytes employing an electroporation step. With respect to the cell used for electroporation, there is no disclosure of electrode surface area. Therefore, and of key importance, cell chamber volume is indeterminable. A broad range of medium conductivities is stated. A broad range of electrode gaps is stated. Yet, there is no teaching provided for choosing any particular set of medium conductivity and electrode gap.

Dimitrov showed that leakage of a fluorescent dye from electroporated red blood cells was less in medium with a moderate conductivity compared to medium with a low conductivity. Using a sensitive assay for permeability of small molecules one group (Pucihar, G et al, Bioelectrochemistry 2001, V 54: 107-115) showed that lowering the conductivity of an electroporation buffer resulted in no change of permeability at given electric fields but an increase in viable cells. The assay used, electroporation using bleomycin, detects small amounts of uptake of small molecules and would not be sensitive to differences in amount of electroporation in a given cell.

Others have found just the opposite effect, such as disclosed in "Better permeability of cells to small molecules was seen during electroporation using media of higher conductivity" (Rols, M P, Tiessie, Eur. J Biochem 1989 V 179:109-115). Rols and Tiessie showed that permeability to a small molecule, Trypan Blue, was greater in high sodium medium at equal field strength and equal number of pulses. Others (vnd den Hoff, M J, Christoffels, V M, Labruyere, W T, Moorman, A F, Lamers, W H, Electrotransfection with "intracellular" buffer, 1995, Methods Mol. Biol. V48:185-197) used high levels of potassium to mimic intracellular ionic content in an effort to preserve cell viability. A more recent study (Baron, S et al, J. Immunol. Meth., 2000 V 242: 115-126) used commercially available medium with a high potassium content (VisSpan, Belzer U W cold-storage solution, DuPont Pharmaceuticals) to increase electroporation efficacy. The material delivered during this study was macromolecules such as proteins and DNA.

None of the above references discussed the use of medium with lower conductivity to achieve the movement of macromolecules into mammalian cells. None of the references discussed the use of medium with lower conductivity to allow the use of larger capacity electrodes.

Other components of the medium contribute both to transfection and to cell viability. One component that has been used is potassium. Potassium in physiological levels equal to intracellular amounts tends to increase viability in electroporated cells. This was shown by van den Hoff (van den Hoff et al., Nucleic Acids Res., vol. 20, No. 11, 1992, p. 2902) and others. The addition of potassium to electroporation medium increases the conductivity of the medium and makes the medium less desirable for use in larger electrodes.

Calcium ions also are reported to increase viability of cells following electroporation. The reason for the increase in viability is reported to be a contribution by calcium in the resealing process after electroporation. The increase in viability due to calcium is slightly offset by decreased uptake of small molecules, presumably by the same mechanism of increased pore closure due to calcium. The increase in viability due to small amounts of calcium (0.1 mM), is obtained at a low cost in terms of increased conductivity because of the small amount used. Therefore, the addition of calcium to electroporation medium is desirable.

Osmolarity of the medium affects cell viability and the efficiency of movement of large molecules through cell membranes. Most electroporation is done using media with normal osmolarity. However, the use of hypoosmolar media can increase the efficiency of DNA transfection. (van den Hoff et al, Nucleic Acids Res., vol. 18, No. 21, 1990, p. 6464) (Golzio et al., Biophys. J., vol. 74, 1998, pp. 3015-3022). Osmolarity can be adjusted in electroporation media using non-ionic compounds such as sugars, sugar alcohols, aminosugars of other non-toxic organic compounds. These materials do not add to the conductivity. Conductivity can be precisely controlled using inorganic anions with inorganic or organic cations. The use of non-ionic organic material to adjust osmolarity without affecting conductivity is desirable.

Other references include:
Melkonyan et al., "Electroporation efficiency in mammalian cells is increased by dimethyl sulfoxide (DMSO)", Nucleic Acids Res., vol. 24, No. 21, 1996, pp. 4356-4357 and Rols et al., "Control by ATP and ADP of voltage-induced mammalian-cell-membrane permeabilization, gene transfer and resulting expression", Eur. J. Biochem., vol. 254, 1998, pp. 382-388.

Other parameters are of interest herein with respect to electroporation methods and apparatus disclosed in the prior art. Of particular interest are the parameters of capacity, environment for cell treatment (static or flow), treated material, whether clinical use is provided for, and media or buffer used. TABLE 4 sets forth a number of U.S. patents with respect to these parameters.

TABLE 4

| Patent | Capacity | Static or flow | Treated material | Clinical use | Media or buffer used |
|---|---|---|---|---|---|
| 4,695,472 | Large | Flow | Food | N | Food |
| 4,695,547 | Small | Static | Cells | N | Any |
| 4,838,154 | Large | Flow | Food | N | Food |
| 4,849,089 | Small | Static | Cells | N | Any |
| 4,882,281 | Small | Static | Cells | N | Any |
| 5,048,404 | Large | Flow | Food | N | Food |
| 5,098,843 | Large | Flow* | Cells | Possibly | Non-Ionic |
| 5,128,257 | Small | Static | Adherent cells | N | Ionic |
| 5,134,070 | Small | Static | Adherent cells | N | Ionic |
| 5,137,817 | Small ** | Static | Cells | Y | Any |
| 5,173,158 | Small | Static (on filter) | Cells | Possibly | Any |
| 5,186,800 | Small | Static | Bacteria | N | Low ionic |
| 5,232,856 | Small | Static | Adherent cells | N | Any |
| 5,235,905 | Large | Flow | Food | N | Food |
| 5,283,194 | Small | Static | Cells | Possibly | Any |
| 5,545,130 | Large | Flow | Blood | Y | Ionic |
| 5,676,646 | Large | Flow | Blood | Y | Ionic |
| 5,720,921 | Large | Flow | Blood | Y | Ionic |
| 5,776,529 | Large | Flow | Food | N | Ionic |
| 5,874,268 | Small | Static | Adherent cells | N | Any |
| 6,001,617 | Small | Static | Adherent cells | N | Any |
| 6,074,605 | Large | Flow | Blood | Y | Ionic |

Notes for TABLE 4:
*Electric field is always on, no pulses, effective pulse width determined by flow rate
** Electrodes plated onto surface More specifically with respect to the patents set forth in TABLE 2, U.S. Pat. No. 4,695,472 describes the treatment of food by electroporation using a large volume flow-through chamber. Cannot reduce conductivity of food, has large effective capacity, no clinical use.

U.S. Pat. No. 4,695,547 describes round electrodes for electroporation within round tissue culture plates. No low conductive medium, no large size, no clinical use.

U.S. Pat. No. 4,838,154 describes the treatment of food by electroporation using a large volume flow-through chamber. Cannot reduce conductivity of food, has large effective capacity, no clinical use.

U.S. Pat. No. 4,849,089 describes round electrodes for electroporation using fully enclosed chambers. No low conductive medium, no large size, no clinical use.

U.S. Pat. No. 4,882,281 describes round electrodes for electroporation within round tissue culture plates. No low conductive medium, no large size, no clinical use.

U.S. Pat. No. 5,048,404 describes the treatment of food by electroporation using a large volume flow-through chamber. Cannot reduce conductivity of food, has large effective capacity, no clinical use.

U.S. Pat. No. 5,098,843 describes a flow through electroporation chamber for transfection of cells. The pulse is always on and the effective pulse width is determined by the time in the chamber (flow rate). Non-ionic medium is described, large volume capacity, possible clinical use but not described.

U.S. Pat. No. 5,128,257 describes an apparatus for transfecting cells grown as adherent cells. Apparatus consists of multiple parallel plates placed on a monolayer of cells. Only buffer described is PBS (highly ionic), large capacity difficult due to monolayer of cells. Clinical use not described.

U.S. Pat. No. 5,134,070 describes a chamber for culturing cells on an optically transparent surface that is conductive. The chamber is for electroporation of the adherent cells. Low-ionic medium is mentioned in the claims but no specific formula is discussed. Large capacity difficult because of adherent cells, no clinical use mentioned.

U.S. Pat. No. 5,137,817 describes a variety of electrodes. The example used non-ionic medium, however it mentions that a variety of different ionic strength media can be used. In vivo and in vitro electrodes are described. The in vitro electrodes are small capacity because they have electrodes plated onto surfaces (not easily scalable). Low ionic medium used, small capacity, clinical uses mentioned for in vivo electrodes.

U.S. Pat. No. 5,173,158 mentions the electroporation of cells that are trapped in pores of a non-conducting membrane. Low voltages are possible because all current flows through the membrane pores. Electroporation medium conductivity or ionic content is not mentioned. No clinical use is mentioned. Small capacity due to the need to trap cells in a pore.

U.S. Pat. No. 5,186,800 describes the transfection of prokaryotes (bacteria). Low ionic medium is used. Does not describe the use of low ionic medium with mammalian cells. States small capacity is desired. No clinical use described.

U.S. Pat. No. 5,232,856 describes electroporation where one electrode is partially conductive. A tilted electrode may be used on one of the electrodes to compensate for the uneven electric fields generated using one partially conductive electrode. Although not clear in the claims, the partially conductive electrode is for adherence of cells to its surface. Ionic content of medium not mentioned. Adherence would limit size. Clinical use is not mentioned.

U.S. Pat. No. 5,235,905 describes the use of electroporation to process liquid food. Large capacity flow through electrode is described. Ionic content of food is not adjustable. Large static capacity is not described. Clinical use is not described.

U.S. Pat. No. 5,283,194 mentions the electroporation of cells that are trapped in pores of a non-conducting membrane. Low voltages are possible because all current flows through the membrane pores. Electroporation medium conductivity or ionic content is not mentioned. No clinical use is mentioned. Small capacity due to the need to trap cells in a pore.

U.S. Pat. No. 5,514,391 describes the use of electroporation to process liquid food. Large capacity flow through electrode is described. Ionic content of food is not adjustable. Large static capacity is not described. Clinical use is not described.

U.S. Pat. Nos. 5,545,130 and 5,676,646 describe a flow through electroporation device. It is designed to treat whole blood. Material can be added to the blood that is not ionic but blood is highly ionic. Large capacity is due to flow through. Low conductivity is not mentioned for increasing capacity. Large static capacity is not described. Clinical use is described.

U.S. Pat. No. 5,720,921 describes a flow through electroporation chamber. A modification is made to add flexible walls to buffer pressure changes. The main example given is to treat red blood cells by introducing material in them that increases the release of oxygen from the cells. An electroporation medium is used that is conductive. Large capacity is due to flow through. Low conductivity is not mentioned for increasing capacity. Large static capacity is not described. Clinical use is described.

U.S. Pat. No. 5,776,529 describes the use of electroporation to process liquid food. Large capacity flow through electrode is described. Ionic content of food is not adjustable. Large static capacity is not described. Clinical use is not described.

U.S. Pat. No. 5,874,268 describes an electroporation chamber designed to electroporated adherent cells. The intent of the invention is to reduce the number of cells needed. Large capacity is not mentioned. Specific electroporation buffers are not mentioned (just a statement about using any electroporation buffer). Clinical use is not described.

U.S. Pat. No. 6,001,617 describes an optically transparent electroporation chamber for treatment of adherent cells. Size is limited by adherent cells. No low ionic medium is discussed. No clinical use is discussed.

U.S. Pat. No. 6,074,605 describes a flow through electroporation chamber. The main example given is to treat red blood cells by introducing material in them that increases the release of oxygen from the cells. An electroporation medium is used that is conductive. Large capacity is due to flow through. Low conductivity is not mentioned for increasing capacity. Large static capacity is not described. Clinical use is described.

Another aspect of the prior art relates to the parameters of conductivity in conjunction with electrode dimensions (height, width, and gap), presence or absence of a cuvette, volume, and dimension, such as shown in TABLE 5.

TABLE 5

Electrode Dimensions
Static, no adherent cells

| Publication | Conductivity (μs/cm) | Electrode Dimensions Height | Width mm | Gap mm | Cuvette mm | Volume ml | Dimension |
|---|---|---|---|---|---|---|---|
| 5,124,259 | High (~10K) | 2 | 87.5 | 4 | N | 0.7 | 0.23 |
| 6,040,184 | Very low | | | | Y | | 0.1-0.4 |
| 6,338,965 | Very low | | | | Y | | 0.1-0.4 |
| 6,368,784 | High (~17K) | | | 4 | | | 0.4 |
| Djuzenova 1996 | Moderate to high (800-14000) | | | 6 | N | 1.2 | 0.3 |
| *Kinosita 1977 | Saline and sucrose | | 5-100 | 2-10 | N, cross section = 50-200 mm^2 | | Not determinable from publication |
| Reimann 1975 | PBS | 30 | 30 | 10 | | | 0.11 |
| Dimitrov 1990 | Low to Moderate (~100-10K) | | | 2 | N | 0.003 | 66 |
| Pucilar 2001 | 0.0011-1.61 S/m | | | 2 | | 0.05 | 0.8 |
| Baron 2000 | High (~17K) | | | 4 | | 0.4 | 0.4 |
| Schwister 1985 | PBS | 30 | 30 | 10 | N | 10 | 0.1 |
| Mussauer 2001 | 1.5-3.5 mS/cm | | | 2 | | 0.4 | 0.1 |
| Mussauer 1999 | 1-8 mS/cm | | | 6 | | 1.1 | 0.33 |
| Fomekong 1998 | 0.064-1.447 S/cm | | | 5 | | 0.884 | 0.28 |
| 5,128,257 | Saline | 10-20 | 50-80 | 0.5-1.5 | | | |
| 5,186,800 | Water | | | 0.5-2.5 | | 0.001-1 | 0.5-hundreds |

Having discussed prior art above, it is clear that the foregoing body of prior art does not teach or suggest electroporation methods and apparatus which have the following combination of desirable features: (1) can be used for clinical and therapeutic purposes wherein all cells, ex vivo or in vitro, are subject to substantially the same process conditions; (2) is scalable so that substantially large volumes of ex vivo or in vitro cells can be processed in a relatively short period of time; (3) achieves increased biological cell capacity without increasing the size of chamber resulting in excessively large amperage requirements; (4) limits heating within the chamber to low levels; (5) exposes substantially all ex vivo or in vitro cells to the same electric field intensity and direction; (6) permits variable rectangular pulse waveforms such as disclosed in U.S. Pat. No. 6,010,613 can be employed; (7) avoids problems in flow through treatment cells that are due to laminar and turbulent flow conditions; (8) permits the use of medium with lower conductivity to achieve the movement of macromolecules into mammalian cells and to allow the use of larger volume chambers; and (9) is easily scalable to large capacity without using a flow through treatment chamber for cells to be treated.

The foregoing desired characteristics are provided by the unique large volume ex vivo electroporation method of the present invention as will be made apparent from the following description thereof. Other advantages of the present invention over the prior art also will be rendered evident.

DISCLOSURE OF INVENTION

In view of the above, it is an object of the present invention is to provide a large volume ex vivo electroporation method which can be used for clinical and therapeutic purposes wherein all cells, ex vivo or in vitro, are subject to substantially the same process conditions.

Still another object of the present invention is to provide a large volume ex vivo electroporation method that is scalable so that substantially large volumes of ex vivo or in vitro cells can be processed in a relatively short period of time.

Yet another object of the present invention is to provide a large volume ex vivo electroporation method, which achieves increased biological cell capacity without increasing the size of the chamber resulting in excessively large amperage requirements.

Even another object of the present invention is to provide a large volume ex vivo electroporation method that limits heating within the treatment cell to low levels.

Still a further object of the present invention is to provide a large volume ex vivo electroporation method which exposes substantially all ex vivo or in vitro cells to the same electric field intensity and direction.

Still another object of the present invention is to provide a large volume ex vivo electroporation method, which permits variable rectangular pulse waveforms such as disclosed in U.S. Pat. No. 6,010,613 can be employed.

Yet another object of the present invention is to provide a large volume ex vivo electroporation method that avoids problems in flow through treatment cells that are due to laminar and turbulent flow conditions.

Still a further object of the present invention is to provide a large volume ex vivo electroporation method that permits the use of medium with lower conductivity to achieve the movement of macromolecules into mammalian cells and to allow the use of larger capacity chambers.

Yet another object of the present invention is to provide a large volume ex vivo electroporation method, which is easily scalable to large capacity without using a flow through treatment chamber for cells to be treated.

These together with still other objects of the invention, along with the various features of novelty, which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

To achieve the foregoing and other advantages, the present invention, briefly described, provides a static chamber with large volume to insure all cells are subject to the same electric field intensity and direction and the density of the cells and material are uniform. With this invention any waveform may be used. This invention is a voltage waveform generator connected to an electrode with parallel plates with has low conductivity media, a cell density of 20 million cells per 10 milliliters or less. The invention uses media with conductivity between 50 µS/cm and 500 µS/cm (which is equal to 50 microSiemens/cm to 500 microSiemens/cm). The invention may be used in clinical applications and has a closed sterile chamber into which the cells and large molecules are inserted and removed.

In accordance with one aspect of the invention, a method is provided of treating vesicles with exogenous material for insertion of the exogenous material into the vesicles includes the steps of:

a. retaining a suspension of the vesicles and the exogenous material in a treatment volume in a chamber which includes electrodes, wherein the chamber has a geometric factor ($cm^{-1}$) defined by the quotient of the electrode gap squared ($cm^2$) divided by the chamber volume ($cm^3$), wherein the geometric factor is less than or equal to 0.1 $cm^{-1}$), wherein the suspension of the vesicles and the exogenous material is in a medium which is adjusted such that the medium has conductivity in a range spanning 50 microSiemens/cm to 500 microSiemens/cm, wherein the suspension is enclosed in the chamber during treatment, and b. treating the suspension enclosed in the chamber with one or more pulsed electric fields, wherein in accordance with a. and b. above, the treatment volume of the suspension is scalable, and wherein the time of treatment of the vesicles in the chamber is substantially uniform.

Preferably, the chamber is a closed chamber. Preferably, the chamber has at least a 2 milliliter capacity. The chamber and the contents thereof can be sterile. Preferably, the chamber includes entry and exit ports for entry and removal of the suspension. Preferably, the electrodes are parallel plate electrodes.

The electric fields are substantially uniform throughout the treatment volume. The electric fields can include a rectangular voltage pulse waveform to produce a uniform pulse electric field between parallel plate electrodes greater than 100 volts/cm and less than 5,000 volts/cm, substantially uniform throughout the treatment volume.

The vesicles can be living cells, i.e., eukaryotes and prokaryotes, and the medium can be a physiological medium and has a conductivity between 50 and 500 µS/cm (which equals 50 microSiemens/cm to 500 microSiemens/cm). The number of living cells that are treated in the chamber at one time can be more than 10 million in number. Furthermore, the number of living cells that are treated in the chamber at one time can be more than 20 million in number.

The vesicles can be autologous cells that are to be returned to a donor after treatment with the exogenous material. The vesicles can be syngeneic cells that are to be given to a recipient other than the donor. The vesicles can be zenogeneic cells. The vesicles can be artificial liposomes.

The pulsed electric fields can be from electrical pulses, which are in a sequence of at least three non-sinusoidal electrical pulses, having field strengths equal to or greater than 100 V/cm, to the material. The sequence of at least three non-sinusoidal electrical pulses has one, two, or three of the following characteristics (1) at least two of the at least three pulses differ from each other in pulse amplitude, (2) at least two of the at least three pulses differ from each other in pulse width, and (3) a first pulse interval for a first set of two of the at least three pulses is different from a second pulse interval for a second set of two of the at least three pulses.

With the method of the invention, the temperature rise during vesicle treatment is miniscule.

The method of the invention, with respect to the chamber volume, is scalable in a range spanning 2 to 10 milliliters. The method of the invention can be carried out in sequential batches.

The exogenous material can be a therapeutic material. The exogenous material can be a therapeutic product formed from the treatment of the vesicles with exogenous material. The exogenous material can be selected from the following group: a polynucleotide; DNA; RNA; a polypeptide; a protein; and an organic compound.

The exogenous material can include numerous base pairs, for example, at least eight base pairs.

With the invention, the chamber has a chamber volume, the suspension has a suspension volume, and the suspension volume is greater than the chamber volume. In this respect, an initial portion of the suspension volume is moved into the chamber, retained and treated in the chamber, and moved out from the chamber. Then, an additional portion of the suspension volume is moved into the chamber, retained and treated in the chamber, and moved out from the chamber.

Still further portions of the suspension volume are sequentially moved into the chamber, retained and treated in the chamber, and moved out from the chamber. These steps can be repeated until the suspension volume is depleted.

In accordance with another aspect of the invention, an electroporation apparatus is provided which includes a chamber which has a chamber volume of at least 2 milliliters. A pair of electroporation electrodes are contained within the chamber. An electroporation medium, carrying vesicles in suspension, is contained in the chamber between the electroporation electrodes. The medium has a conductivity between 50 microSiemens/cm and 500 microSiemens/cm. A source of pulsed voltages is electrically connected to the electroporation electrodes, and means for adding material to the chamber for electroporation treatment therein. Also, means are provided for removing treated material from the chamber.

Preferably, sealing means are connected to the chamber for providing a sealed chamber. The sealing means can include a quantity of elastomer material.

Preferably, the sealed chamber is sterile inside the chamber. Preferably, the chamber includes vent means for venting air when fluid is moved into the chamber. The vent means can include a filter member in a wall of the chamber. Alternatively, the vent means can include a vent cell in fluid communication with the chamber.

The chamber includes a chamber inlet and a chamber outlet. A first reservoir can be provided in fluid communication with the chamber inlet, for containing the vesicle-bearing electroporation medium prior to introduction into the chamber. A second reservoir can be provided in fluid communication with the chamber inlet, for containing a chamber flushing material for flushing treated vesicle-bearing medium out from the chamber. A third reservoir can be provided in fluid communication with the chamber outlet, for receiving treated, vesicle-bearing medium that is flushed out from the chamber.

The first reservoir, the second reservoir, and the third reservoir can be comprised of flexible bags. An inlet valve can be connected between the chamber inlet and the first reservoir and the second reservoir, and an outlet valve can be connected between the chamber outlet and the third reservoir.

BRIEF DESCRIPTION OF DRAWINGS

The invention will be better understood and the above objects as well as objects other than those set forth above will become more apparent after a study of the following detailed description thereof. Such description makes reference to the annexed drawing wherein.

MODES FOR CARRYING OUT THE INVENTION

As previously described a significant problem is the conductivity of the media used in electroporation. In the process of the invention, a low conductivity medium is employed to keep the total resistance of the suspension greater than one ohm, wherein heating in the chamber is limited to low levels. Not just any medium conductivity can be used. As the ionic content of the medium is reduced, the number of free ions that are available to build charge (voltage) across the cell member is decreased. The effect is to increase the amount of time it takes to charge the membrane. This process is described by the equation in Electroporation and Electrofusion in Cell Biology, edited by Eberhard Neumann, Arthur Sowers, and Carol Jordan, Plenum Press, 1989, on page 71. Assuming a typical cell diameter of 10 microns, the charging time is 20 microseconds at 80 µS/cm. Below 80 µS/cm the charging time become too long and the pathways in cell membrane stop forming. The TABLE 6 below illustrates the resistance of the media as a function of electrode chamber volume and conductivity.

TABLE 6

| Chamber | Suspension Resistance - ohms | | |
|---|---|---|---|
| Volume ml | 17,000 µS/cm | 200 µS/cm | 80 µS/cm |
| 0.5 | 19.2 | 160 0 | 4000 |
| 1 | 9.6 | 800 | 2000 |
| 5 | 1.92 | 160 | 400 |
| 10 | 0.96 | 80 | 200 |
| 50 | 0.19 | 16 | 40 |

Ex vivo electroporation has been demonstrated in numerous published research projects. At this point commercial applications, such as clinical transfection to produce a vaccine for the patient, requires large electrodes or chambers to process millions of cells at one time. The static parallel plate chamber provides the most uniform amplitude and most uniform electric field direction of any configuration available. This uniformity is required to insure uniform treatment of the target cells. It is also important not to use very high-density cell concentration such as 30 million cells/ml to insure local uniform electric fields about the cells. This invention applies to chambers in a range spanning 2 to 10 milliliters.

Using larger chambers results in high current flow when voltage is applied. The equations for chamber resistance vs. conductivity of the cell and media mixture and the chamber dimensions are as follows:

$$\text{Volume of material} = l \times A$$

$$\text{Resistance of Material} = \rho\frac{l}{A} = \frac{1}{\sigma}\frac{l}{A} = \frac{1}{\sigma}\frac{l^2}{\upsilon} = \frac{GF}{\sigma} \text{ ohms}$$

$\rho$=resistivity in ohm-cm $\sigma=1/\rho$ in Siemens/cm $\upsilon$=volume of material being treated l=gap between electrodes (cm)

A=area of electrode (cm$^2$)

There is a Geometric Factor (GF), which is a constant for any chamber dimension. As the volume of the chamber gets larger the resistance of the material in the chamber gets smaller thus increasing current flow.

The present invention uses an electrode with large capacity in combination with an electroporation buffer of defined low conductivity. This process exposes all cells to the same treatment conditions, provides control over the amperage required and can process large numbers of cells. Since the cell suspension statically remains in the chamber during application of pulsed electric fields, complex waveforms can be used.

Another aspect of the invention further increases capacity by alternately filling and emptying the gap between the electrodes. In this manner, all desired properties are met during a specific treatment and the electrodes can be re-used for subsequent treatments in a sequential batch process.

Figure 2:
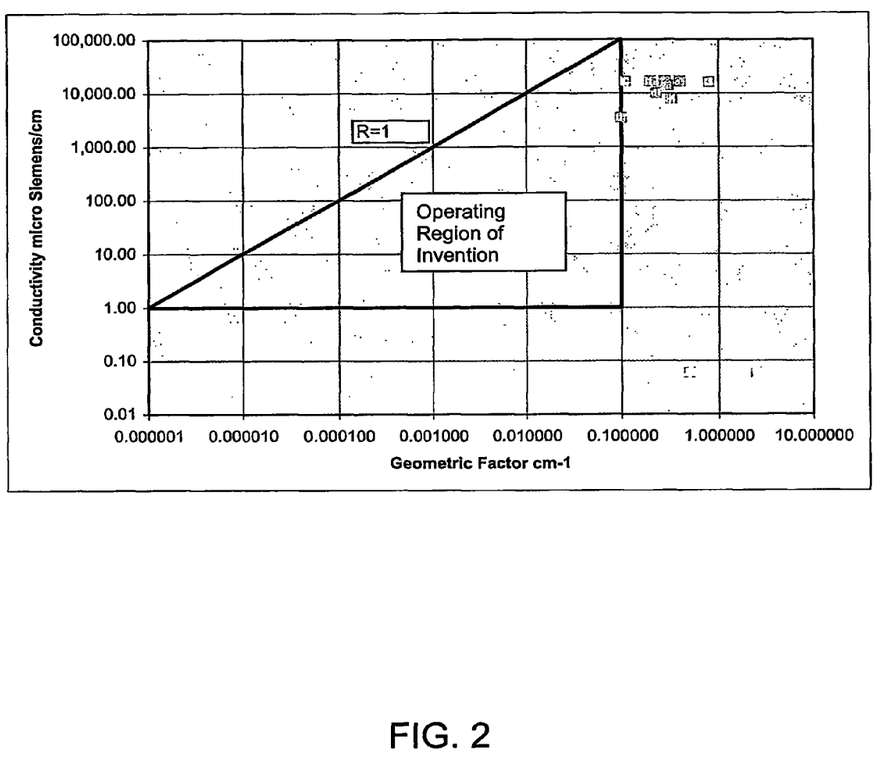
FIG. 2 is a graph illustrating the operating range of the method of the invention, inside the triangle, and how the operating range of the invention is outside operating ranges of prior art electroporation methods, indicated by small blocks outside the triangle.

This present invention specifies a range of medium and suspension conductivities, which can be used versus the chamber dimensions, the larger the volume the smaller the conductivity. This invention specifies an operating area for use with the larger volume chambers. This is illustrated in FIG. 2. Operating points of prior art published results are also presented in FIG. 2 as squares. For chambers with a Geometric Factor less than 0.1 there are two limiting factors, which are related. The first is the absolute value of the chamber resistance. In this invention the chamber resistance is one ohm or greater. Operating below one ohm is viewed as impractical. The other constraint is the conductivity of the medium and suspension in the chamber. As the conductivity decreases the charging time of the cell membrane increases because there are fewer ions external to the cell membrane.

The relationship between the Transmembrane Voltage (TMV) and conductivity and cell diameter is as follows, taken from Newman et al stated below:

Transmembrane Voltage=TMV $TMV=-1.5Er|\cos \delta|f(\lambda)$ where: E=electric filed in volts/cm
r=cell radius in cm
$\delta$=angle from electric field line in degrees $f(\lambda)$ = composite conductivity $$f(\lambda) = \frac{\lambda_o \lambda_1 \left(2\frac{d}{r}()\right)}{(2\lambda_o + \lambda_i)\lambda_m + \left(2\frac{d}{r}\right)(\lambda_o - \lambda_m)(\lambda_i - \lambda_m)}$$

where: $\lambda_o$=conductivity of media external to cell milliSiemens/cm
$\lambda_i$=conductivity of cytoplasm
$\lambda_m$=conductivity of cell membrane
d=thickness of cell membrane Reference: Electroporation and Electrofusion in Cell Biology
Edited by Eberhard Neumann, Arthur Sowers, and Carol Jordon
Plenum Press, 1989

Below 1 microSiemens/cm there are so few ions that the time to change the cell membrane is unrealistically large.

The preferred operating region of the present invention is then:
Cell diameter>1 micrometer
Chamber volume 2 to 10 milliliters
Conductivity of Material to be treated 50 microSiemens/cm to 500 microSiemens/cm
Total resistance of material to be treated in chamber>1 ohm
Geometric Factor of Chamber<0.1 cm$^{-1}$ The invention uses a static chamber with large volume to insure that all cells in suspension are subject to the same electric field intensity and direction and the density of the cells and treating material are uniform. With this invention any waveform may be used. This invention includes a voltage waveform generator connected to electrodes in the form of parallel plates, and, which has a low conductivity medium and a suspension in the static chamber, having a cell density of 20 million cells or less.

A component of the invention is the use of low conductivity medium within a defined range to limit amperage and heat while simultaneously providing enough ions to effectively electroporate cells. Typically the medium used will have a conductivity in a range spanning 50 microSiemens/cm to 500 microSiemens/cm.

The invention may be used in clinical applications and with a closed sterile chamber into which the cells and large molecules are inserted and removed.

One aspect of the invention further increases capacity by alternately filling and emptying the chamber. In this manner, all desired properties are met during a specific treatment and the chamber can be re-used for subsequent treatments in a sequential batch process.

The conductivity of the medium used in electroporation is an important aspect of this invention. In this process, a low conductivity medium is employed to keep the total resistance of the medium small and virtually eliminate heating. There is a limit to the lower conductivity medium that can be used. As the ionic content of the medium is reduced the number of free ions that are available to build charge (voltage) across the cell membrane is decreased. The effect is to increase the amount of time it takes to charge the membrane. This process is described by the equation in Neumann, p 71. Assuming a typical cell diameter of 10 microns, the charging time is 20 microseconds at a conductivity of 80 microSiemens/cm. For a typical cell diameter of 10 microns, below 80 microSiemens/cm, the charging time becomes too long and the pathways in cell membranes stop forming.

Using an electrode with a 4 mm gap, TABLE 6 illustrates the resistance of the medium as a function of electrode chamber volume and conductivity.

Figure 1A:
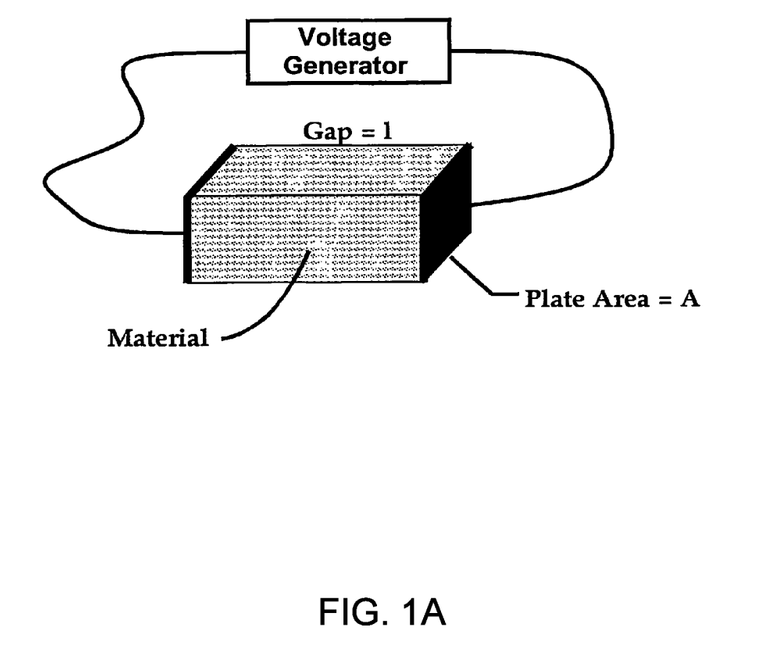
FIG. 1A is a schematic illustration of apparatus employed with carrying out the method of the invention.
Figure 1B:
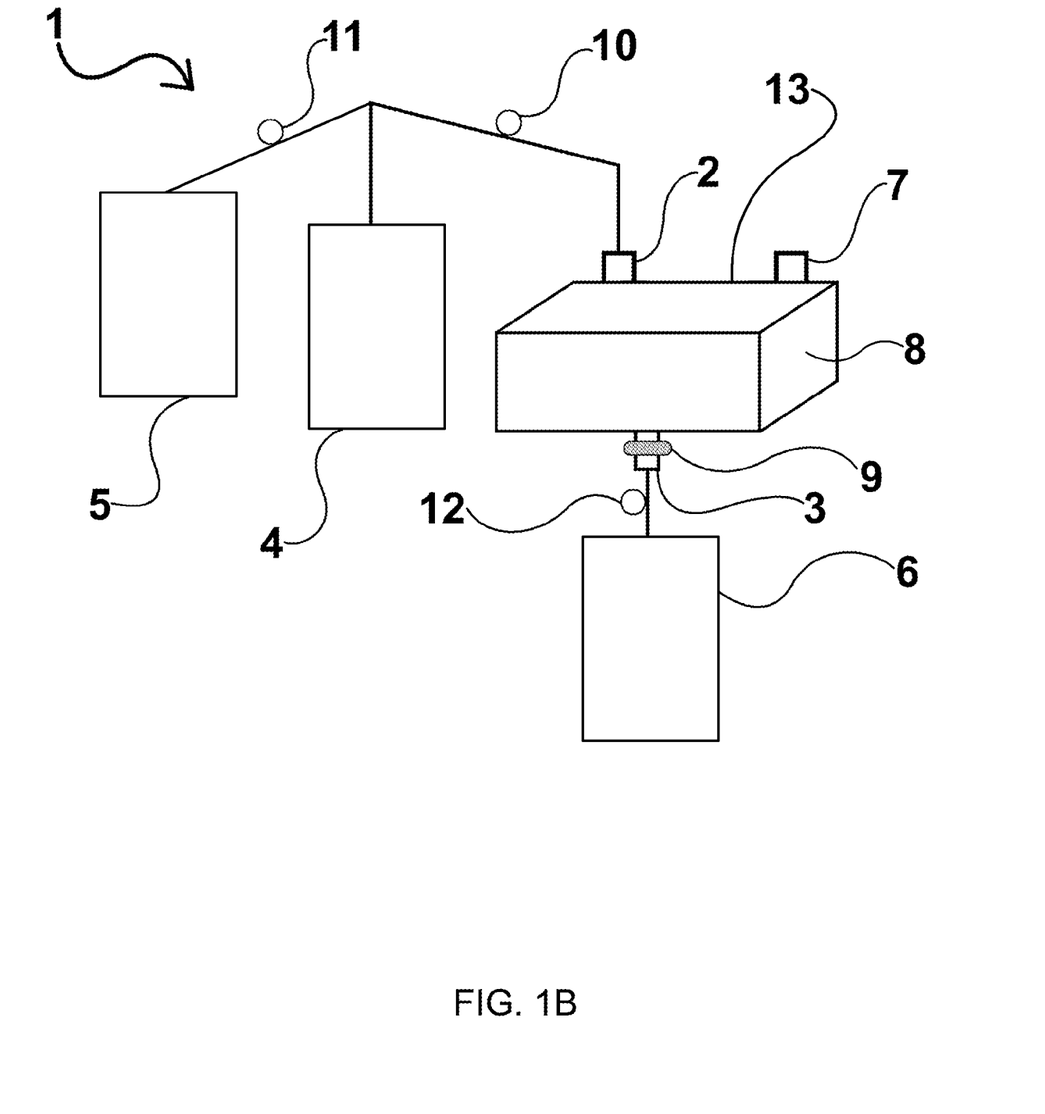
FIG. 1B is a schematic illustration of the electroporation chamber with its parts of the electroporation apparatus.

In one aspect of the invention, a chamber with two electrodes is used as shown in FIG. 1. An example of electrode dimensions that can be used is a gap of 0.4 cm, electrode height of 2 cm and electrode length of 10 cm. The chamber can be used with a commercial electroporator such as the Cyto Pulse Sciences, Inc. PA-4000 electroporator.

Figure 3:
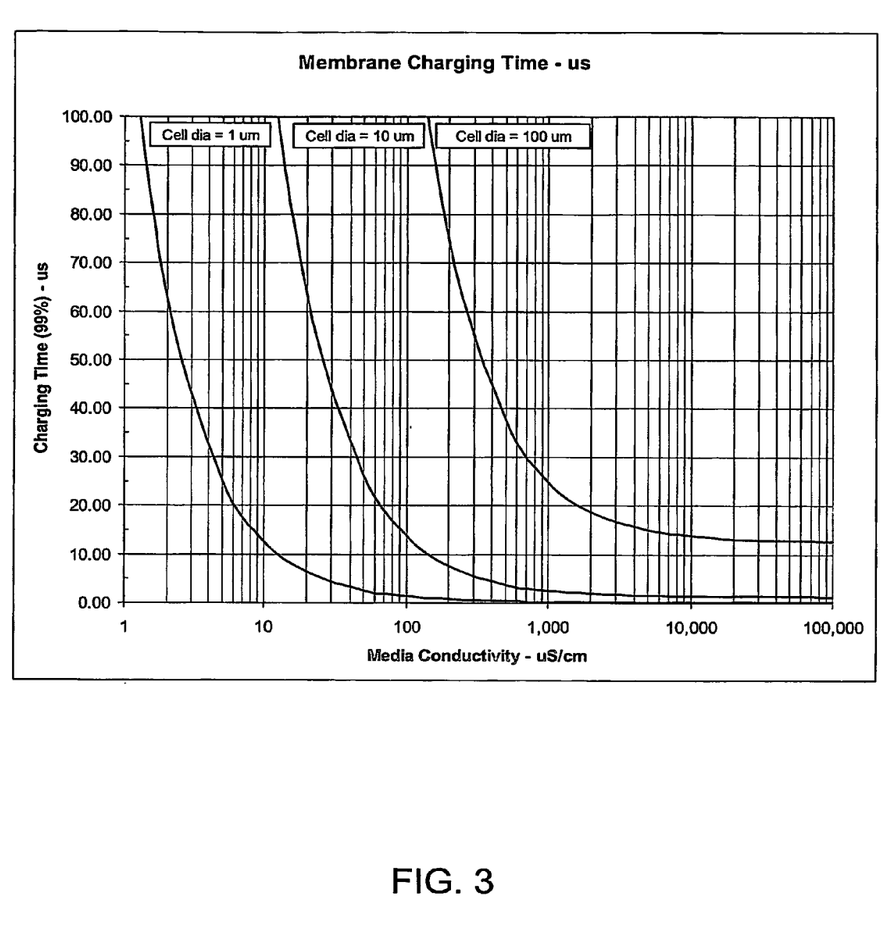
FIG. 3 is a graph illustrating the relationship between charging time (in microseconds) of biological cells and media conductivity (in microSiemens/cm) for cells having three different diameters, namely 1 micrometer, 10 micrometers, and 100 micrometers.
Figure 4:
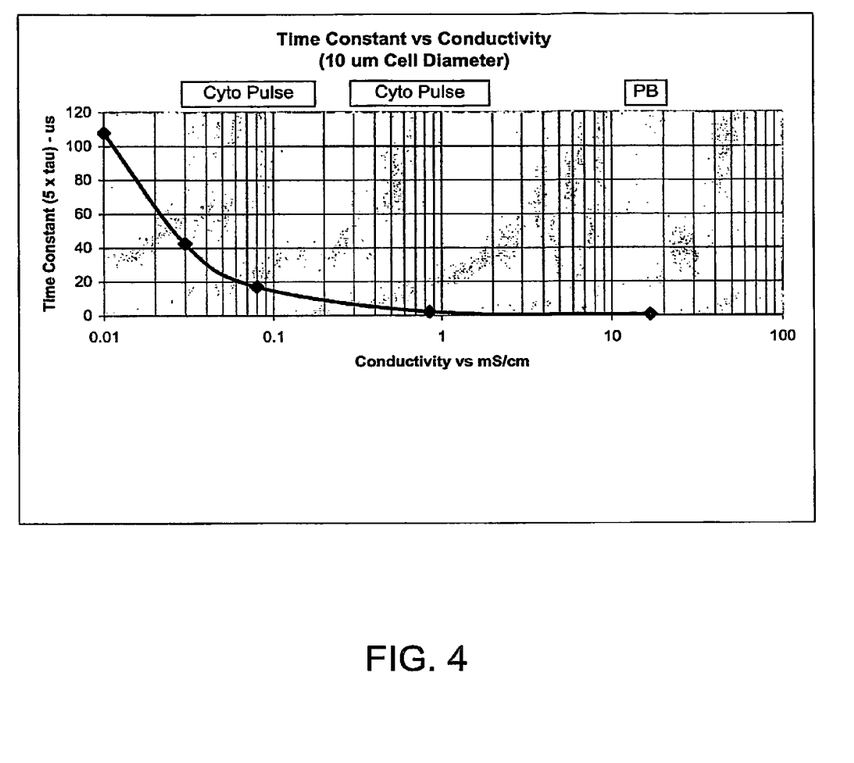
FIG. 4 is a graph showing Time Constant versus Conductivity as it relates to the method of the invention.

An example of a medium that can be used with the chamber is one with the following formula:
Sorbitol 280 millimoles
Calcium Acetate, 0.1 millimoles
Magnesium Acetate, 0.5 millimoles FIG. 3 is a graph illustrating the relationship between charging time (in microseconds) of biological cells and media conductivity (in microSiemens/cm) for cells having three different diameters, namely 1 micrometer, 10 micrometers, and 100 micrometers. From FIG. 3 it is clear that for media conductivity below 1 microSiemen/cm, the charging time would be so large that electroporation would not work.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a large volume ex vivo electroporation method which may advantageously be used for clinical and therapeutic purposes wherein all cells, ex vivo or in vitro, are subject to substantially the same process conditions. With the invention, a large volume ex vivo electroporation method is provided which is scalable from 2 to 10 milliliters so that substantially large volumes of ex vivo or in vitro cells can be processed in a relatively short period of time. With the invention, a large volume ex vivo electroporation method is provided which achieves increased biological cell capacity without increasing the size of a chamber resulting in excessively large amperage requirements. With the invention, a large volume ex vivo electroporation method is provided which limits heating within the chamber to low levels. With the invention, a large volume ex vivo electroporation method is provided which exposes substantially all ex vivo or in vitro cells to the same electric field intensity and direction. With the invention, a large volume ex vivo electroporation method provides that the density of the material to be inserted into the treatment chamber can be held constant. With the invention, a large volume ex vivo electroporation method is provided which permits variable rectangular pulse waveforms such as disclosed in U.S. Pat. No. 6,010,613 can be employed. With the invention, a large volume ex vivo electroporation method is provided which avoids problems in flow through treatment cells that are due to laminar and turbulent flow conditions. With the invention, a large volume ex vivo electroporation method is provided which permits the use of medium with lower conductivity to achieve the movement of macromolecules into mammalian cells and to allow the use of larger capacity chambers. With the invention, a large volume ex vivo electroporation method is provided which is easily scalable to large capacity without using a flow through treatment chamber for cells to be treated.

The electroporation chamber with its parts 1 as shown by FIG. 1B includes the electroporation chamber 13 with a geometric factor defined by the quotient of the electrode gap squared (cm$^2$) divided by the chamber volume (cm$^3$), wherein the geometric factor is less than or equal to 0.1 cm$^{-1}$. The chamber 13 has an inlet 2 and an outlet 3 configured for sequential passage of suspensions and fluids during electroporation. The chamber 13 includes a first reservoir 4 in fluid communication with the inlet 2 for containing the suspensions and fluids prior to introducing into the chamber 13 for treatment, a second reservoir 5 in fluid communication with the inlet 2 for containing flushing material for flushing the suspensions and fluids after treatment out from the chamber 13, and a third reservoir 6 in fluid communication with the outlet 3 for receiving the suspensions and fluids flushed after treatment out from the chamber 13. The inlet valve 10 is connected between the inlet 2 and the first reservoir 4 and the inlet valve 11 is connected between the second reservoir 5 and inlet 2, and the outlet valve 12 is connected between the outlet 9 and the third reservoir 6. The chamber 13 includes the vent 7 for removing air when the chamber is filled with a fluid. The chamber includes sealing means 9 for providing a sealed chamber. The chamber 13 includes parallel plate electrodes 8. Not shown by FIG. 1B, the chamber 13 includes a source of pulsed voltages electrically connected to said parallel plate electrodes 8 configured to provide pulse waveforms and an uniform electric field between the parallel plate electrodes 8, wherein the uniform electric field is greater than 100 volts/cm and less than 5,000 volts/cm and substantially uniform throughout the chamber 13.

With respect to the above description, it should be realized that the optimum dimensional relationships for the parts of the invention, to include variations in size, form function and manner of operation, assembly and use, are deemed readily apparent and obvious to those skilled in the art, and therefore, all relationships equivalent to those illustrated in the drawings and described in the specification are intended to be encompassed only by the scope of appended claims.

While the present invention has been shown in the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed is:
1. An apparatus for electroporation comprising:
a sterile electroporation chamber with a geometric factor defined by the quotient of the electrode gap squared (cm$^2$) divided by the chamber volume (cm$^3$), wherein the geometric factor is less than or equal to 0.1 cm$^{-1}$;
wherein the chamber is configured for sequential electroporation and the chamber has an inlet and an outlet configured for sequential passage of suspensions and fluids during electroporation;

the chamber comprising:
- a first reservoir in fluid communication with the inlet for containing the suspensions and fluids prior to introducing into the chamber for treatment, a second reservoir in fluid communication with the inlet for containing flushing material for flushing the suspensions and fluids after treatment out from the chamber, and a third reservoir in fluid communication with the outlet for receiving the suspensions and fluids after treatment flushed out from the chamber;
- a vent for removing air when the chamber is filled with a fluid;
- parallel plate electrodes; and
- a source of pulsed voltages electrically connected to said parallel plate electrodes configured to provide pulse waveforms and an uniform electric field between the parallel plate electrodes, wherein the uniform electric field is greater than 100 volts/cm and less than 5,000 volts/cm and substantially uniform throughout the chamber.

2. The apparatus of claim 1, wherein the vent is a filter member in the wall of the chamber.

3. The apparatus of claim 1, wherein the vent is a vent-cell in fluid communication with the chamber.

4. The apparatus of claim 1, wherein the chamber further comprises an elastomeric seal.

5. The apparatus of claim 1, wherein the first reservoir contains a low conductivity medium for suspending vesicles for electroporation, wherein the conductivity of the medium is between 50 microSiemens/cm and 500 microSiemens/cm.

6. The apparatus of claim 1, wherein the volume of the chamber is between 2 ml and 10 ml.

7. The apparatus of claim 1, wherein the first reservoir, the second reservoir, and the third reservoir comprise flexible bags.

8. The apparatus of claim 1, wherein an inlet valve is connected between the chamber inlet and the first reservoir and the second reservoir, and an outlet valve is connected between the chamber outlet and the third reservoir.

* * * * *